US009200232B2

(12) United States Patent
Kolb et al.

(10) Patent No.: US 9,200,232 B2
(45) Date of Patent: Dec. 1, 2015

(54) RHEOLOGICAL METHODS TO DETERMINE THE PREDISPOSITION OF A POLYMER TO FORM NETWORK OR GEL

(75) Inventors: Rainer Kolb, Kingwood, TX (US); Sudhin Datta, Houston, TX (US); Pritesh A. Patel, Novato, CA (US); Kirk A. Nass, San Francisco, CA (US)

(73) Assignees: ExxonMobil Chemical Patents Inc., Houston, TX (US); Chevron Oronite Company LLC, Richmond, CA (US)

( * ) Notice: Subject to any disclaimer, the term of this patent is extended or adjusted under 35 U.S.C. 154(b) by 394 days.

(21) Appl. No.: 13/605,677

(22) Filed: Sep. 6, 2012

(65) Prior Publication Data
US 2013/0085092 A1    Apr. 4, 2013

Related U.S. Application Data

(60) Provisional application No. 61/540,997, filed on Sep. 29, 2011.

(51) Int. Cl.
*C10L 1/18* (2006.01)
*C10L 1/16* (2006.01)
*C10M 143/08* (2006.01)
*G01N 11/16* (2006.01)
*G01N 11/00* (2006.01)

(52) U.S. Cl.
CPC ..... *C10M 143/08* (2013.01); *C10M 2205/0285* (2013.01); *C10N 2230/02* (2013.01); *G01N 11/16* (2013.01); *G01N 2011/0033* (2013.01)

(58) Field of Classification Search
CPC .......................... C10M 171/00; C10M 143/08
USPC .......................... 508/269, 591, 466
See application file for complete search history.

(56) References Cited

U.S. PATENT DOCUMENTS

| 5,112,510 A | 5/1992 | Rossi |
| 7,053,153 B2 * | 5/2006 | Schauder ............ 525/191 |
| 2002/0028860 A1 | 3/2002 | Kerr et al. |
| 2003/0050387 A1 | 3/2003 | Fujisawa |
| 2008/0188386 A1 * | 8/2008 | Burrington et al. ......... 508/382 |
| 2010/0105597 A1 | 4/2010 | Harrington et al. |

FOREIGN PATENT DOCUMENTS

| WO | WO-2010/126720 A1 | 11/2010 |
| WO | WO-2010/126721 A1 | 11/2010 |
| WO | WO-2010/129151 A1 | 11/2010 |

* cited by examiner

*Primary Examiner* — Prem C Singh
*Assistant Examiner* — Francis C Campanell
(74) *Attorney, Agent, or Firm* — Novak Druce Connolly Bove + Quigg LLP

(57) ABSTRACT

A method is provided to determine the predisposition of a polymer to form network or gel in a lubricating oil which comprises obtaining a composition of a polymer in a diluent, measuring the shear stress as a function of shear rate, determining the yield stress using the Herschel-Bulkley equation and assessing the yield stress. A method is also provided to determine the predisposition of a polymer to form network or gel in a lubricating oil which comprises obtaining a composition of a polymer in a diluent, determining at least one of (i) the storage modulus G' and loss modulus G" of the composition by subjecting the composition to sinusoidal (oscillating) stress or strain of certain amplitude and frequency, (ii) the phase lag (angle) of the response strain or stress δ, or (iii) the tangent (tan) δ, and (c) assessing at least one of the G', G", δ, or tan(δ) determined.

7 Claims, 7 Drawing Sheets

RHEOLOGICAL METHODS TO DETERMINE THE PREDISPOSITION OF A POLYMER TO FORM NETWORK OR GEL

CROSS REFERENCE TO RELATED APPLICATIONS

This application claims priority to U.S. Provisional Application No. 61/540,997 filed on Sep. 29, 2011, the entire contents of which is hereby incorporated by reference. This application is related to co-pending U.S. application Ser. No. 12/761,880 and Ser. No. 12/762,096 which in turn claim the priority to and the benefit from U.S. Ser. No. 61/173,528, filed on Apr. 28, 2009, and U.S. Ser. No. 61/173,501, filed on Apr. 28, 2009, and U.S. Ser. No. 12/569,009, filed on Sep. 29, 2009, all of which are incorporated herein by reference in their entirety. This application is also related to U.S. Ser. No. 61/299,816, filed Jan. 29, 2010, and U.S. Ser. No. 61/297,621, which are herein incorporated by reference in their entirety.

TECHNICAL FIELD

The method of the present disclosure is to screen for polymers having a tendency to form gels. The present disclosure relates to methods to determine the predisposition of a polymer to form networks or gels in diluents such as oils, especially lubricating oils. It has been found according to the present disclosure that a procedure selected from the group of yield stress test and G'/G" crossover test as modified according to this disclosure can be used to determine whether or not a polymer has a tendency to gel.

BACKGROUND OF DISCLOSURE

Viscosity Index Improvers (VII) are polymers that influence rheological properties of the lubricating oil by, for example, interactions with components of lubricating oils (e.g., base oil, pour point depressant (PPD), dispersant or detergent inhibitor (DI) package) and/or interactions with itself (polymer-polymer). VII interactions with lubricating oil components (e.g., wax) are well characterized by tests like Mini-Rotary Viscometer (MRV) (ASTM D4684), Pour Point (ASTM D5949, D5950, or D5985), and Scanning Brookfield (ASTM D5133).

Viscosity index improvers are typically polymeric molecules that are added to compositions such as a lubricating oil to alter viscosity response of the composition with temperature. With lubricating oils, these molecules thicken the oil at higher temperatures offsetting viscosity losses that would otherwise reduce the lubricating properties and wear protection of the oil and increase boundary friction. At low temperature, however, these polymers may form networks due to polymer entanglements or small crystals. The extent to which such networks are formed depends on the temperature, concentration, and the nature and molecular weight of the polymer. Such networks can "stiffen" the lubricating oil and reduce its flowability, form 'lumps' or 'gels,' or turn the entire solution into a 'frozen' solid (composition that can not be poured).

Certain VII having a high amount of continuous ethylene segments dispersed in the polymer backbone can lead to gelation via polymer network formation. Olefin copolymers such as ethylene-propylene copolymers, for example, tend to stiffen due to crystallization of the ethylene segments of the polymer chain. Other, non-crystalline molecules can form gels or become frozen solid when the polymer forms stable entanglements. Certain VII containing styrene blocks also lead to network formation by polymer interactions. Both effects depend on the molecular weight of the polymer and its concentration and temperature of the solution.

Polymer interactions are different than wax interactions in base oils and require different measurement technique(s). Methods mentioned above such as Mini-Rotary Viscometer (MRV), Pour Point, and Scanning Brookfield are not sufficiently sensitive or indicative of how polymers such as alpha-olefin copolymers would interact in lubricating oils. There is currently a need for a test that would reliably detect the predisposition of a given polymer to form gels or turn into solids when formulated into a composition.

SUMMARY OF DISCLOSURE

One aspect of the present disclosure relates to a method to determine the predisposition of a polymer to form a network or gel in a composition such as a lubricating oil, which comprises (a) obtaining a composition of a polymer in a diluent, (b) measuring the shear stress of the composition as a function of shear rate or measuring the shear rate of the composition as a function of shear stress, (c) determining the yield stress using the Herschel-Bulkley equation:

$$\tau = \tau_0 + k(\delta)^n$$

where,
$\tau$=Shear Stress
$\tau_0$=Yield Stress
k=consistenc y
$\gamma$=shear rate
and n=power law exponent, and (d) comparing the yield stress, thereby determining the predisposition of the polymer to form a network or gel. The Herschel-Bulkley equation is well-known in the art and explained, for example, in Bird, R. B.; Armstrong, R. C.; Hassager, O. Dynamics of Polymeric Liquids; John Wiley & Sons: New York, 1987; Vol. 1.

Another aspect of the present disclosure relates to a method to determine the predisposition of a polymer to form a network or gel in a composition such as a lubricating oil which comprises (a) obtaining a composition of a polymer in a diluent, (b) determining at least one of (i) the storage modulus G' and loss modulus G" of the composition by subjecting the composition to sinusoidal (oscillating) stress or strain of certain amplitude and frequency, (ii) the phase lag (angle) of the response strain or stress $\delta$, or (iii) the tangent (tan) $\delta$, and assessing at least one of the G', G", $\delta$, or tan($\delta$) determined, thereby determining the predisposition of the polymer to form a network or gel, wherein $\delta$ is the phase lag angle for the composition to respond to the sinusoidal stress or strain.

Still other objects and advantages of the present disclosure will become readily apparent by those skilled in the art from the following detailed description, wherein it is shown and described only the preferred embodiments. As will be realized, the disclosure is capable of other and different embodiments, and its several details are capable of modifications in various obvious respects, without departing from the disclosure. Accordingly, the description is to be regarded as illustrative in nature and not as restrictive.

PREFERRED EMBODIMENTS OF THE INVENTION

Figure 1:
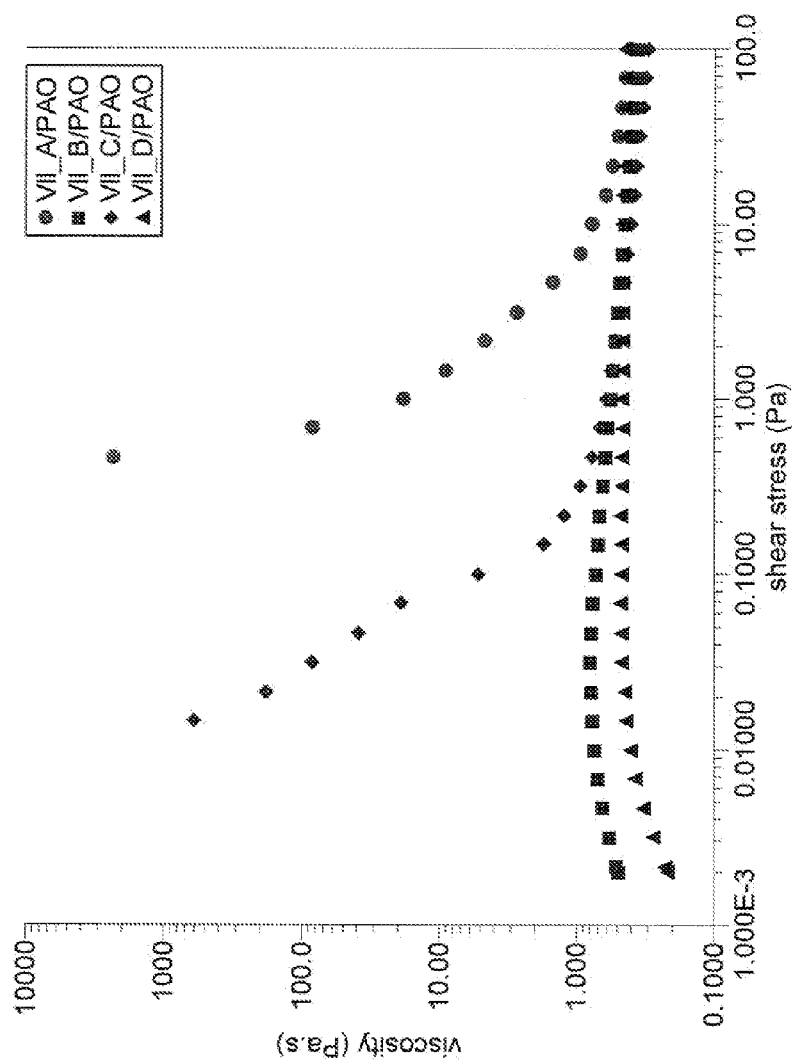
FIG. 1 is a plot showing viscosity versus shear stress measurements carried out according to the present disclosure.

The present disclosure provides improved rheological method(s) to characterize polymer interactions leading to gel formation in diluents, oils, and in particular lubricating oils using Steady State Flow Rheology or Oscillatory Rheology. The rheological methods according to the present disclosure can be used to design polymer having optimized properties as Viscosity Index Improvers in lubricating oils.

The methods of the present disclosure are especially useful in evaluating copolymers of alpha-olefins, such as ethylene-propylene copolymers, and compositions thereof. For example, the methods of the disclosure can be used to evaluate polymer compositions comprising two types of ethylene copolymer. The polymer composition can have a first ethylene copolymer having relatively lower ethylene content (compared to the second ethylene copolymer) and which is a copolymer of ethylene, an alpha-olefin comonomer, and optionally an internal olefin and optionally a polyene, such as a diene. The polymer composition can have a second ethylene copolymer having relatively higher ethylene-content copolymer (compared to the first ethylene copolymer) and which is a copolymer of ethylene, an alpha-olefin and optionally a polyene such as a diene. In one instance, the polymer composition can comprise a first ethylene copolymer, preferably at least 30 wt. %, 35 wt. %, 40 wt. %, 45 wt. %, 50 wt. %, or 51 wt. % of a first ethylene copolymer based on the weight of the polymeric composition, and a second ethylene copolymer, preferably 70 wt. %, 65 wt. %, 60 wt. %, 55 wt. %, 50 wt. %, or 49 wt. % or less of a second ethylene copolymer based on the weight of the polymer composition. In some embodiments, the polymer compositions being evaluated comprise from about 51% to about 60%, about 70%, or about 80% the first ethylene copolymer, and from about 49% to about 20%, about 30%, or about 40% of the second ethylene copolymer, by weight of the polymer composition. Additional exemplary polymer compositions can be found in, for example, International Applications WO 10/126,720, WO 10/126,721, and WO10/129151, incorporated herein by reference in their entirety.

The diluent or oil according to the instant disclosure may be derived from natural lubricating oils, synthetic lubricating oils or mixtures thereof. Suitable base oil includes base stocks obtained by isomerization of synthetic wax and slack wax, as well as hydrocrackate base stocks produced by hydrocracking (rather than solvent extracting) the aromatic and polar components of the crude. Suitable base oils include those in all API categories I, II, III, IV and V as defined in API Publication 1509, Appendix E, 15th Edition, April 2002. Saturates levels and viscosity indices for Group I, II and III oils are listed in Table 1. Group IV oils are polyalphaolefins (PAO). Group V oils include all other oils not included in Group I, II, III, or IV.

TABLE 1

Saturates, Sulfur and Viscosity Index of Group I, II, III, IV and V Base Stocks

| Group | Saturates (As determined by ASTM D2007) Sulfur (As determined by ASTM D2270) | Viscosity Index (As determined by ASTM D4294, ASTM D4297 or ASTM D3120) |
|---|---|---|
| I | Less than 90% saturates and/or Greater than to 0.03% sulfur | Greater than or equal to 80 and less than 120 |
| II | Greater than or equal to 90% saturates and less than or equal to 0.03% sulfur | Greater than or equal to 80 and less than 120 |
| III | Greater than or equal to 90% saturates and less than or equal to 0.03% sulfur | Greater than or equal to 120 |
| IV | All Polyalphaolefins (PAOs) | |
| V | All others not included in Groups I, II, III, or IV | |

Natural lubricating oils may include animal oils, vegetable oils (e.g., rapeseed oils, castor oils and lard oil), petroleum oils, mineral oils, and oils derived from coal or shale.

Synthetic oils may include hydrocarbon oils and halo-substituted hydrocarbon oils such as polymerized and inter-polymerized olefins, alkylbenzenes, polyphenyls, alkylated diphenyl ethers, alkylated diphenyl sulfides, as well as their derivatives, analogues and homologues thereof, and the like. Synthetic lubricating oils also include alkylene oxide polymers, interpolymers, copolymers and derivatives thereof wherein the terminal hydroxyl groups have been modified by esterification, etherification, etc. Another suitable class of synthetic lubricating oils comprises the esters of dicarboxylic acids with a variety of alcohols. Esters useful as synthetic oils also include those made from about $C_5$ to about $C_{12}$ monocarboxylic acids and polyols and polyol ethers. Tri-alkyl phosphate ester oils such as those exemplified by tri-n-butyl phosphate and tri-iso-butyl phosphate are also suitable for use as oils.

Silicon-based oils (such as the polyalkyl-, polyaryl-, polyalkoxy-, or polyaryloxy-siloxane oils and silicate oils) comprise another useful class of synthetic lubricating oils. Other synthetic lubricating oils include liquid esters of phosphorus-containing acids, polymeric tetrahydrofurans, polyalphaolefins, and the like.

The oil may be derived from unrefined, refined, rerefined oils, or mixtures thereof. Unrefined oils are obtained directly from a natural source or synthetic source (e.g., coal, shale, or tar sand bitumen) without further purification or treatment.

Examples of unrefined oils include a shale oil obtained directly from a retorting operation, a petroleum oil obtained directly from distillation, or an ester oil obtained directly from an esterification process, each of which may then be used without further treatment. Refined oils are similar to the unrefined oils except that refined oils have been treated in one or more purification steps to improve one or more properties. Suitable purification techniques include distillation, hydrocracking, hydrotreating, dewaxing, solvent extraction, acid or base extraction, filtration, and percolation, all of which are known to those skilled in the art. Rerefined oils are obtained by treating used oils in processes similar to those used to obtain the refined oils. These rerefined oils are also known as reclaimed or reprocessed oils and often are additionally processed by techniques for removal of spent additives and oil breakdown products.

Oil derived from the hydroisomerization of wax may also be used, either alone or in combination with the aforesaid natural and/or synthetic oil.

Such wax isomerate oil is produced by the hydroisomerization of natural or synthetic waxes or mixtures thereof over a hydroisomerization catalyst.

The typical alpha olefin used as a comonomer with ethylene are from $C_3$ to about $C_{20}$ alpha-olefins such as propylene, 1-butene, 1-pentene, 1-hexene, 1-octene of styrene. Propylene is preferred comonomer. The polymer backbone is the ethylene copolymer or terpolymer of $C_3$ to about $C_{20}$ alpha-olefins. The terpolymer variations may contain about 0.1 to 10 mole percent of conjugated diene or triene. The polymerization reaction used to form the ethylene-alpha-olefin copolymer backbone is generally carried in presence of Ziegler-Natta or metallocene catalyst system.

A visual gel test used to test for gellation is described below. This test involves preparing a solution of the polymer to be tested, and placing about a 10 ml sample of the solution into 40 ml glass vial with screw cap. A typical vial is available from VWR Corporation as catalog number (VWR cat #: C236-0040). The sample is then heated in an 80° C. oven for about 1 hour to remove any thermal history. The vial is stored at 10° C.±5° C. for 4-6 hr in a Low Temperature Incubator. A typical incubator is available from VWR corporation as catalog number 35960-057. The vial is then stored at −15° C.+/−0.5° C. overnight in a chest freezer. A typical chest freezer is Revco Model UTL 750-3-A30. A thermocouple is placed into a reference vial, identical to the sample but containing only the solvent or base oil to monitor the actual sample temperature. After 16 hours remove the vial from the freezer, do not remove the cap and immediately tilt the vial 80-90 degrees to an almost horizontal position. If condensation forms on the outside of the vial quickly wipe the vial with a paper towel. The test is carried out for multiple cycles. The samples are rated twice a week up to 8 weeks with final ratings as follows:

No Gel—free flowing liquid

Very Light Gel—minor surface texture

Light Gel—rough surface

Medium Gel—visible lumps

Heavy Gel—large visible lumps

The following visual grading can be used to rate the sample visually.

TABLE 2

| GRADE | DESCRIPTION | DETAILED COMMENTS |
|---|---|---|
| 0 | No gel | Free flowing fluid with mirror surface |
| 1 | Light gel | Slight non-homogeneity, surface roughness |
| 2 | Medium gel | Large non-homogeneity, slight pulling away from vial |
| 3 | Heavy gel | Pulls away from vial, large visible lumps |
| 4 | Solid | Solid gel |

The following oil compositions were used in testing according to the present disclosure.

The VII/poly-alpha-olefin (PAO) solutions contain 2.4 wt % polymer in 4 cSt PAO lubricating oil to measure the interactions. No wax interference was observed during testing.

10W-50 formulations in Group I/III/PAO base oils were used. The polymer interaction was measured in the final oils. High polymer content, 10W-50, lubricating oils were used to amplify the rheological response of the VII interactions.

Experimental polymers for evaluation are shown in Table 3. Samples designated VII-A, VII-B, VII-C and VII-D are ethylene-propylene copolymers with their respective ethylene contents provided below.

TABLE 3

|  | VII-A | VII-B | VII-C | VII-D |
|---|---|---|---|---|
| % Ethylene (wt %) | 64 | 64 | 64 | 62 |
| SSI, % (ASTM D6298) | 24.0 | 24.0 | 27 (est.) | 24.4 |

PAO solutions containing the test polymers and the resulting properties of the oils are shown in Table 4.

TABLE 4

|  | Oil 1 | Oil 2 | Oil 3 | Oil 4 |
|---|---|---|---|---|
| VII | A | B | C | D |
| Concentration, wt % | 2.4 | 2.4 | 2.4 | 2.4 |
| Kinematic Viscosity (KV) at 100° C., cSt | 16.6 | 16.8 | 17.4 | 15.3 |
| Gel-cycle ratings | Heavy | No | Medium | No |

10W-50 lubricating oils containing the test polymers and the resulting properties of the oils are shown in Table 5.

TABLE 5

|  | Oil 5 | Oil 6 | Oil 7 |
|---|---|---|---|
| DI Package | 13.0 | 13.0 | 13 |
| Base Oils (Group I, III, IV), wt % | 70.7 | 70.7 | 70.7 |
| PPD, wt % | 0.3 | 0.3 | 0.3 |
| VII-type | VII-A | VII-B | VII-D |
| VII, wt % | 16 | 16 | 16 |
| Kinematic Viscosity at 100° C., cSt | 18.05 | 18.06 | 17.90 |
| Cold Cranking Simulator Viscosity @−25° C., cP | 6627 | 6706 | 7417 |
| MRV @-30° C., cP | 30603 | 48237 | 44518 |
| Scanning Brookfield, Gelation Index | 8.6 | 12.2 | 8.0 |

The present disclosure makes it possible to significantly reduce the testing time. The present disclosure provides for highly sensitive torque and displacement measurements and provides torque measurement resolution as low as $10^{-2}$ μN-m and displacement resolution of 25 nrad. The techniques provide for precise temperature (peltier plate) and shear rate (about 10 decades) control. An advantage of the present disclosure is the ability to use a small quantity of a sample (~5 ml). The methods of the present disclosure are suitable for various geometries/fixtures for a wide variety of compositions, especially lubricating oils According to the present disclosure, yield stress is determined. Yield stress is typically measured at 0° C. and −15° C., by steady state flow method by varying stress from about 100 Pa to about $10^{-5}$ Pa. Generally, the stress/shear rate curve fits the Herschel-Bulkley equation.

Figure 2:
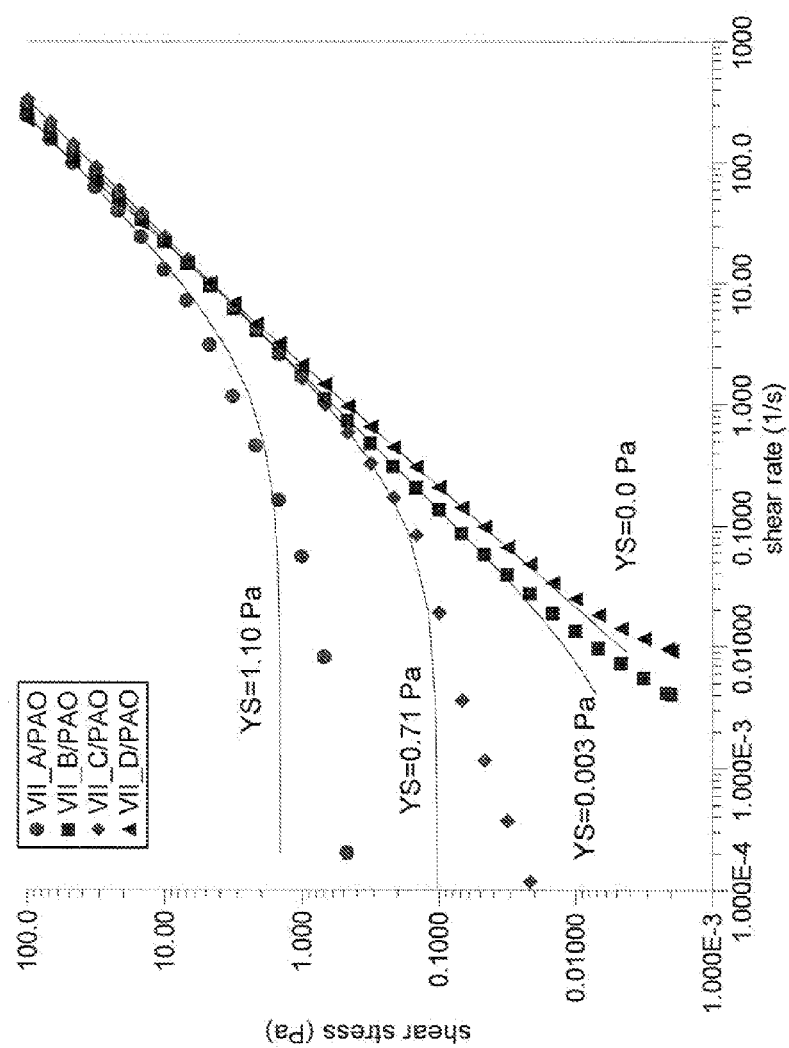
FIG. 2 is a plot showing shear stress versus shear rate measurements carried out according to the present disclosure.

In particular, a steady state uni-directional rotation is used at the specified temperature. The shear rate or shear stress is varied and the shear stress or shear rate is measured (e.g. see FIG. 2) and the viscosity is calculated (e.g. see FIG. 1). A sample profile of 60 mm, 2°2'01" steel cone geometry is typically employed with a gap of 54 μm between the plates. The testing is carried out by equilibrating the device at 40° C., cooling to 0° C. (at ~20° C./min), ramping the stress from 100 Pa to $2 \times 10^{-3}$ Pa, cooling to −15° C. (at ~20° C./min), and ramping the stress from 100 Pa to $2 \times 10^{-3}$ Pa.

With respect to flow measurements of VII/PAO solutions; VII OCPs of the same overall ethylene content have different responses in steady state flow rheology (e.g. see FIG. 1). The method of the present disclosure can be used to characterize the polymer-polymer interactions in lubricating oil.

Yield stress is calculated using the Herschel-Bulkley equation.

$$\tau=\tau_0+k(\gamma)^n$$

where,
  τ=Shear Stress
  $\tau_0$=Yield Stress
  k=consistency
  γ=shear rate
  and n=power law exponent Not all high ethylene OCPs are same. The calculated yield stress are 3-4 orders of magnitude different depending on the polymer design even at same ethylene content (e.g. see FIG. 2). The above described gel-cycle test can be carried out to develop a standard. As shown in the table below generally, the yield stress calculated by Herschel-Bulkley model to fit shear stress-shear rate response of VII/PAO solutions correlates with the gel-cycle test rating of its corresponding 10W-50 lubricating oil. The table can be used as a standard to compare the results from a yield stress test to determine whether a particular polymer is likely or not to form a gel in lubricating oil.

TABLE 6

| Gel-cycle Method Ratings | Yield Stress (Pa) |
|---|---|
| Heavy Gel | 0.8-4 |
| Medium Gel | 0.05-0.8 |
| Light Gel | 0.02-0.05 |
| No Gel | Below 0.01 Pa |

It is noted that polymer interactions are an order of magnitude lower than the interactions present in lubricating oil system (base oil/VII/PPD/DI) (For example, MRV measures yield stress only above 35 Pa).

Figure 3:
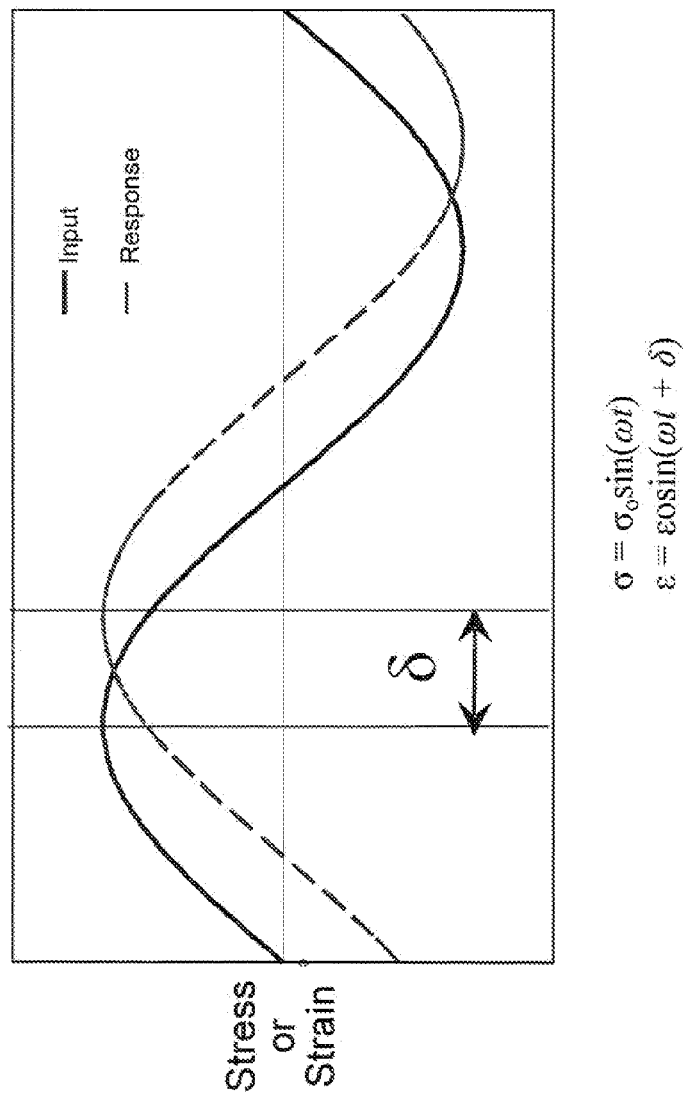
FIG. 3 is a plot of a response strain or stress curve versus time (output) to an applied sinusoidal stress or strain of certain amplitude and frequency (input) as measured by oscillatory rheology carried out according to the present disclosure.

The storage modulus G' and loss modulus G" of the composition to be tested are determined by oscillatory rheology. Sinusoidal stress or strain of certain amplitude and frequency is applied and the corresponding sinusoidal strain or stress response is measured to calculate δ as follows (e.g., see FIG. 3), $$\sigma=\sigma_0 \sin(\omega t)$$

$$\epsilon=\epsilon_0 \sin(\omega t+\delta)$$

where,
  σ=applied stress
  $\sigma_0$=applied stress amplitude
  ε=measured strain
  $\epsilon_0$=strain amplitude
  ω=frequency
  t=time
  δ=phase lag The temperature, strain or stress amplitude, and frequency can be varied. The storage modulus and loss modulus are measured. See FIG. 3.

$$G' = \frac{\text{Stress}}{\text{Strain}} \times \cos(\delta)$$

$$G'' = \frac{\text{Stress}}{\text{Strain}} \times \sin(\delta)$$

A sample profile of 60 mm, 2°2'01" steel cone geometry is used with a gap of 54 μm between the plates. The testing is carried out by equilibrating the device at 40° C. The temperature is ramped from 40° C. to −19° C. at an oscillatory stress of 0.2 Pa and 1 rad/s frequency. The testing is carried out by equilibrating the device at −19° C. The temperature is ramped from 40° C. to −19° C. at an oscillatory stress of 0.2 Pa and 1 rad/s frequency.

The oscillatory rheology measures various rheological parameters, such as storage modulus, G', loss modulus, G", δ or tan(δ), gel-point (G'=G"), parameters that can characterize polymer-polymer interactions in lubricating oil.

Figure 4:
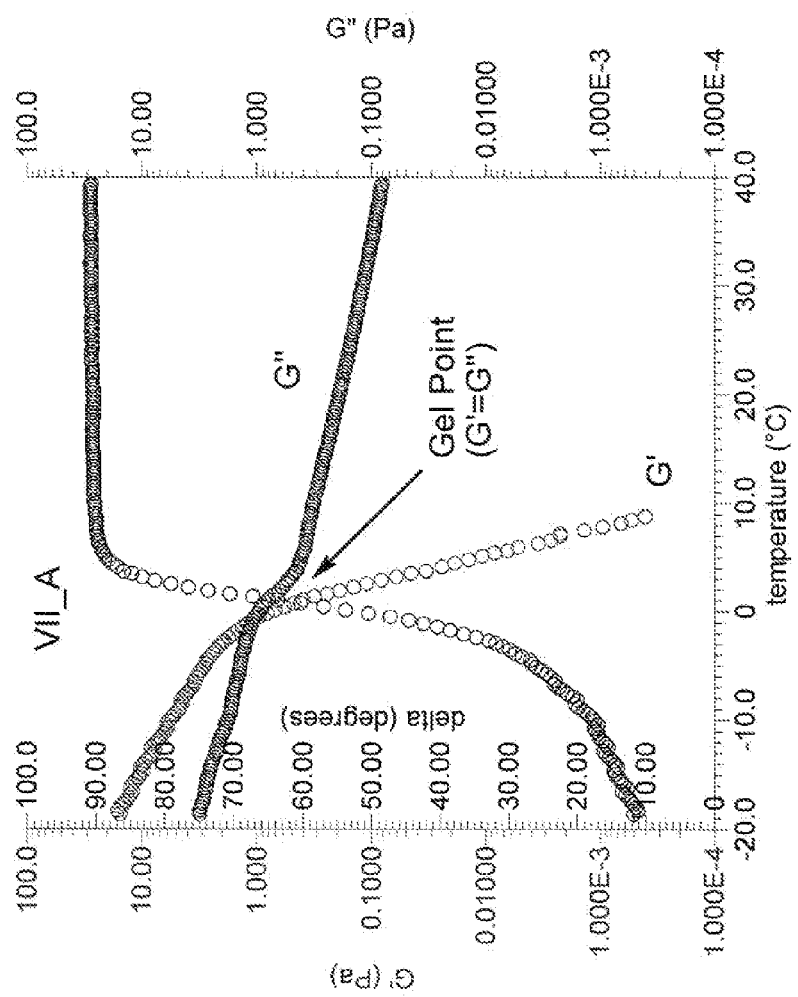
FIGS. 4 and 5 are plots of storage modulus G' and loss modulus G" versus temperature carried out according to the present disclosure.
Figure 5:
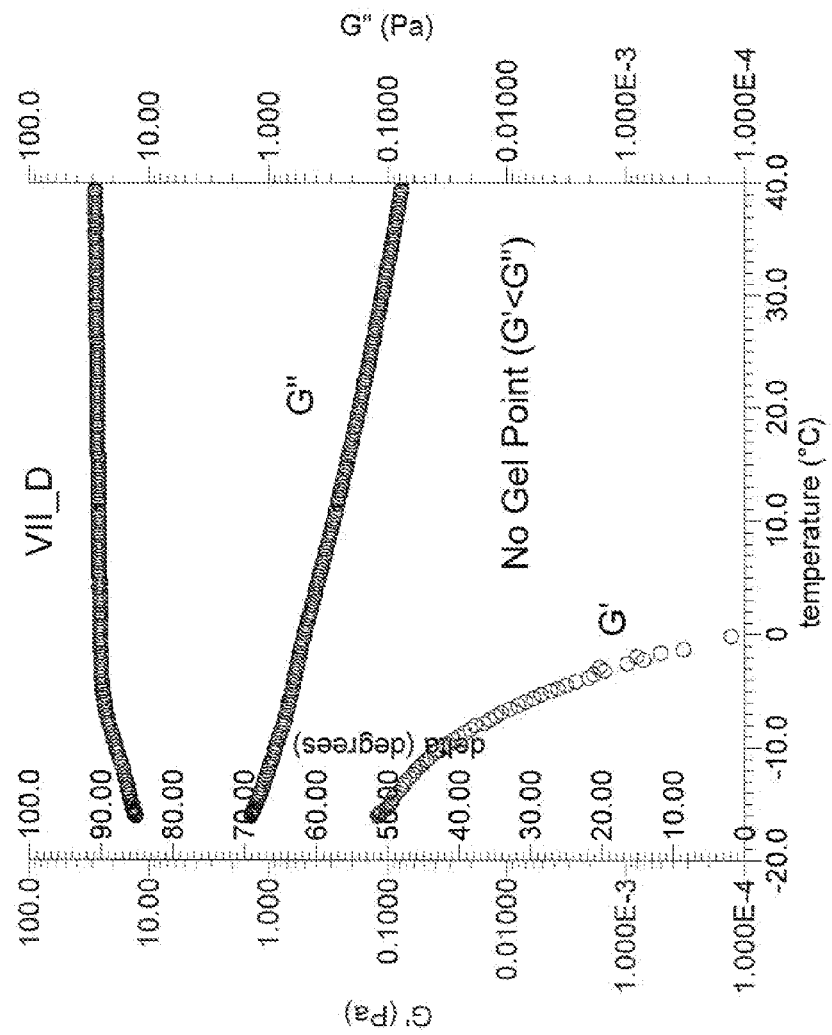

Oscillatory measurements of VII/PAO solutions: Gel-Point and delta (δ). Oil rated as heavy gel in the gel-cycle test also exhibits a gel-point (G'≥G", δ≤45°) in the oscillatory rheology method. Additional parameters such as delta, δ, at given temperature (e.g., at −15° C.) or tan(δ) characterize polymer-polymer interactions. (e.g. see FIGS. 4 and 7).

Figure 6:
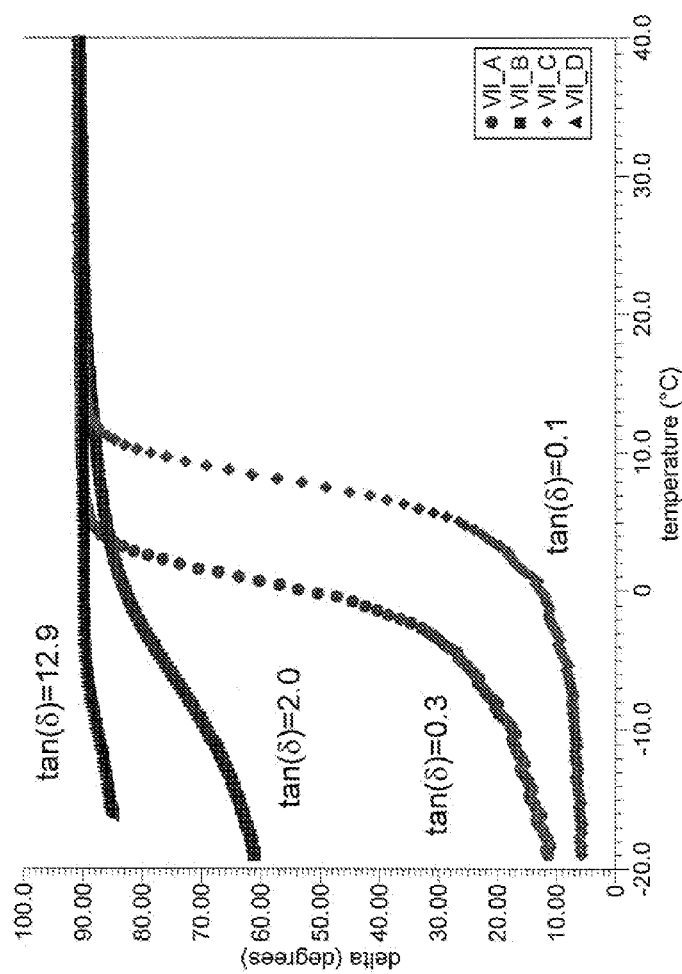
FIG. 6 is a plot of delta δ versus temperature measurements carried out according to the present disclosure. Tan(δ) values listed in the figure are at −15° C.

Oscillatory Measurements of VII/PAO Solutions: Oscillatory rheology can be used to select VII molecules with desired structure-performance in lubricating oils. (see FIG. 6).

The crossover point of G' and G" is the gel point that indicated heavy gelation. However, the information concerning the crossover point of G' and G" is not necessarily sufficient to determine whether in a particular system, polymer interaction not rising to the level of heavy gelation is likely to occur. According to the present disclosure, it has been found that δ or tan(δ), measured by the oscillatory rheology, further quantifies VII interactions. For instance, it has been determined that a tan(δ) greater than 2.0 indicates the formation of networks at a lower level than the heavy gelation identified by the crossover point of G' and G". See FIG. 6. Thus, the δ or tan(δ) can be used to select VII which do not exhibit gelation at low temperatures in lubricating oils.

Figure 7:
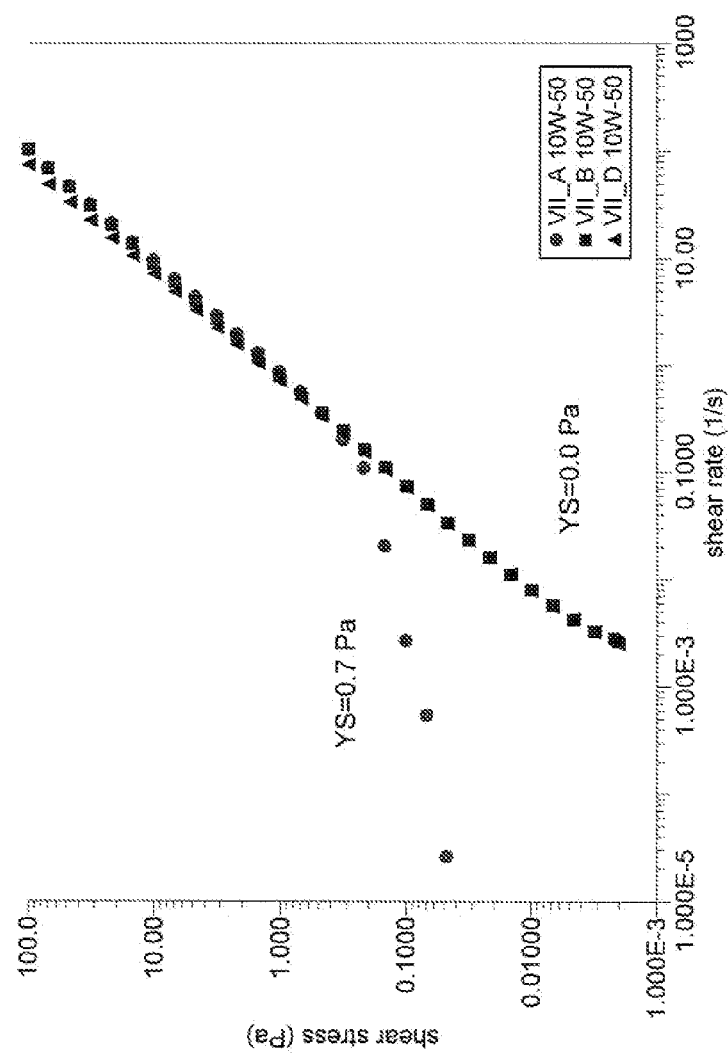
FIG. 7 is another plot showing shear stress versus shear rate measurements carried out according to the present disclosure.

FIG. 7 illustrates that the magnitude of yield stress in high VII content 10W-50 lubricating oils is $10^{-2}$ times lower compared to 2.4 wt % VII/PAO solutions.

Exemplary embodiments of the invention include:
A. A method to determine the predisposition of a polymer to form network or gel in a composition, comprising the steps of:
  (a) obtaining a composition of a polymer in a diluent,
  (b) measuring the shear stress of the composition as a function of shear rate or measuring the shear rate of the composition as a function of shear stress,
  (c) determining the yield stress using the Herschel-Bulkley equation:

$$\tau=\tau_0+k(\gamma)^n$$

where,
    τ=Shear Stress
    $\tau_0$=Yield Stress
    k=consistency
    γ=shear rate
    and n=power law exponent, and
  (d) comparing the yield stress, thereby determining the predisposition of the polymer to form a network or gel.
B. The method according to Embodiment A, wherein the diluent comprises a lubricating oil and the polymer is an alpha-olefin copolymer.
C. The method according to any of Embodiments A and B, wherein the lubricating oil contains a Group I, II, III, IV or V base oil.
D. A method to determine the predisposition of a polymer to form network or gel in a composition, comprising the steps of:
  (a) obtaining a composition of a polymer in a diluent, and
  (b) determining at least one of (i) the storage modulus G' and loss modulus G" of the composition by subjecting the composition to sinusoidal (oscillating) stress or strain of certain amplitude and frequency, (ii) the phase lag (angle) of the response strain or stress δ, or (iii) the tangent (tan) δ, and assessing at least one of the G', G", δ, or tan(δ) determined, thereby determining the predisposition of the polymer to form a network or gel.

E. The method according to Embodiment D, wherein the diluent comprises a lubricating oil and the polymer is an alpha-olefin copolymer.

F. The method according to any of Embodiments E and E, wherein the lubricating oil contains a Group I, II, III, IV or V base oil.

G. The method according to any of Embodiments A-F, wherein the polymer is an ethylene copolymer having an ethylene content of at least about 50 wt. %, by weight of the ethylene copolymer.

H. The method according to any of Embodiments A-G, wherein the polymer is a polymer composition that comprises at least 30 wt. %, based on the weight of the polymer composition, of a first copolymer of ethylene and an alpha-olefin comonomer, and 70 wt. % or less, based on the weight of the polymer composition, of a second copolymer of ethylene and an alpha-olefin comonomer, wherein the first copolymer has a lower ethylene content than the second copolymer.

I. The method according to any of Embodiments A-H, further comprising selecting the polymer for use in a lubricating oil composition.

J. The method according to Embodiment I, further comprising forming a lubricating oil composition comprising the polymer.

K. A lubricating oil composition comprising a polymer selected according to the method of Embodiment J.

M. A method to determine the predisposition of a test polymer to form gel in a composition, comprising the steps of:
(a) forming a sample composition comprising a sample polymer and a diluent,
(b) determining the yield stress of the sample composition,
(c) determining the gellation level of the sample composition,
(d) obtaining a correlation between yield stress with the gellation level of the sample composition to obtain a standard,
(d) obtaining a test polymer,
(e) determining the yield stress of the test polymer,
(f) applying the correlation obtained in step (d) to determine the predisposition of the polymer to form a network or gel.

N. The method of Embodiment N, further comprising the step of (g) selecting the polymer for use in a lubricating oil composition, and forming a lubricating oil composition comprising the polymer.

O. The method of Embodiment G, wherein the ethylene copolymer is an ethylene/propylene copolymer.

The term "comprising" (and its grammatical variations) as used herein is used in the inclusive sense of "having" or "including" and not in the exclusive sense of "consisting only of" The terms "a" and "the" as used herein are understood to encompass the plural as well as the singular.

All publications, patents and patent applications cited in this specification are herein incorporated by reference, and for any and all purpose, as if each individual publication, patent or patent application were specifically and individually indicated to be incorporated by reference. In the case of inconsistencies, the present disclosure will prevail.

The foregoing description of the disclosure illustrates and describes the present disclosure. Additionally, the disclosure shows and describes only the preferred embodiments but, as mentioned above, it is to be understood that the disclosure is capable of use in various other combinations, modifications, and environments and is capable of changes or modifications within the scope of the concept as expressed herein, commensurate with the above teachings and/or the skill or knowledge of the relevant art.

The embodiments described hereinabove are further intended to explain best modes known of practicing it and to enable others skilled in the art to utilize the disclosure in such, or other, embodiments and with the various modifications required by the particular applications or uses. Accordingly, the description is not intended to limit it to the form disclosed herein. Also, it is intended that the appended claims be construed to include alternative embodiments.

What is claimed is:

1. A method to determine the predisposition of a polymer to form network or gel in a composition by polymer-polymer interaction, comprising the steps of:
   (a) obtaining a composition consisting essentially of a polymer in a diluent, wherein the polymer is at least one alpha-olefin copolymer, and
   (b) determining at least one of (i) the phase lag (angle) of the response strain or stress δ, or (ii) the tangent (tan) δ of the composition by subjecting the composition to sinusoidal (oscillating) stress or strain of certain amplitude and frequency, and
   (c) assessing at least one of the (i) δ or (ii) tan(δ) determined, thereby determining the predisposition of the polymer to form a network or gel, whereby when at least one of δ is >60° or tan(δ) is >2, determining that said polymer has a reduced predisposition to form a network or gel by polymer-polymer interaction.

2. The method according to claim 1, wherein the diluent comprises a lubricating oil and the polymer is an alpha-olefin copolymer.

3. The method according to claim 1, wherein the diluent contains a Group I, II, III, IV or V base oil.

4. The method according to claim 1, wherein the polymer is an ethylene copolymer having an ethylene content of at least about 50 wt. %, by weight of the ethylene copolymer.

5. The method according to claim 1, wherein the polymer is a polymer composition that comprises at least 30 wt. %, based on the weight of the polymer composition, of a first copolymer of ethylene and an alpha-olefin comonomer, and 70 wt. % or less, based on the weight of the polymer composition, of a second copolymer of ethylene and an alpha-olefin comonomer, wherein the first copolymer has a lower ethylene content than the second copolymer.

6. The method of claim 1, further comprising selecting the polymer for use in a lubricating oil composition, and forming a lubricating oil composition comprising the polymer.

7. A lubricating oil composition comprising a polymer selected according to the method of claim 6.

* * * * *